United States Patent [19]

Oshlack et al.

[11] 4,443,428

[45] Apr. 17, 1984

[54] EXTENDED ACTION CONTROLLED RELEASE COMPOSITIONS

[75] Inventors: Benjamin Oshlack, New York, N.Y.; Stewart T. Leslie, Aberdeen, Scotland

[73] Assignee: Euroceltique, S.A., Luxembourg

[21] Appl. No.: 390,540

[22] Filed: Jun. 21, 1982

[51] Int. Cl.³ .................. A61K 9/22; A61K 9/24; A61K 9/52

[52] U.S. Cl. ............................ 424/22; 424/19; 424/21; 424/35; 424/38

[58] Field of Search ................... 424/19–22, 424/36, 38

[56] References Cited

U.S. PATENT DOCUMENTS

| 3,525,790 | 8/1970 | Halpern | 424/180 |
|---|---|---|---|
| 3,608,063 | 9/1971 | Banker | 424/22 |
| 3,957,995 | 5/1976 | Amsalem | 424/253 |
| 3,965,256 | 6/1976 | Leslie | 424/19 |
| 4,049,791 | 9/1977 | Cohen | 424/22 |
| 4,116,241 | 9/1978 | Theewes et al. | 424/15 |
| 4,138,475 | 2/1979 | McAinsh et al. | 424/19 |
| 4,160,020 | 7/1979 | Ayer et al. | 424/21 |
| 4,160,452 | 7/1979 | Theewes | 424/21 |
| 4,179,497 | 12/1979 | Cohen et al. | 424/19 |
| 4,235,870 | 11/1980 | Leslie | 424/38 |
| 4,248,858 | 2/1981 | Guley et al. | 424/19 |
| 4,304,765 | 12/1981 | Shell et al. | 424/14 |

OTHER PUBLICATIONS

Sims et al., Chem. Abstr. 85, #51681k, (1976).
Dasta et al., Chem. Abstracts 91, #78812g, (1979).
Cros et al., Chem. Abstracts 83, #120762k, (1975).
Makhkamov et al., Chem. Abstracts 86, #195167r, (1977).

Primary Examiner—Shep K. Rose
Attorney, Agent, or Firm—Steinberg & Raskin

[57] ABSTRACT

The action of controlled release medications is extended by incorporation into the controlled release matrix for a medication a mixture of the salt form of the medication with the free base form of the medication in a proportion of a 75–25% by weight of the salt form to 25–75% by weight of the free base form, the weight amounts being calculated with respect to the active base.

9 Claims, No Drawings

EXTENDED ACTION CONTROLLED RELEASE COMPOSITIONS

BACKGROUND OF THE INVENTION

It is known in the pharmaceutical art to prepare a compositions which provide for slow release of pharmacologically active substances contained in said compositions after oral administration to humans and animals. Such slow release compositions are used to delay absorption of a medicament until it has reached certain portions of the alimentary tract. Such controlled release of a medicament in the alimentary tract further maintains a desired concentration of said medicament in the blood stream for a longer duration than would occur if conventional rapid release dosage forms are administered.

Slow release formulations known in the art include specially coated pellets, coated tablets and capsules wherein the slowed release of the active medicament is brought about through selective breakdown of the coating of the preparation or through compounding with a special matrix to affect the release of a drug. Some slow release formulations provide for related sequential release of a single dose of an active compound at predetermined periods after administration.

It is the intent of all slow release preparations to provide a longer period of pharmacologic response after the administration of a drug than is ordinarily experienced after the administration of the rapid release dosage forms. Such longer periods of response provides for many inherent therapeutic benefits that are not achieved with corresponding short acting, immediate release preparations. Thus, therapy may be continued without interrupting the sleep of the patient, which is of special importance when treating an epileptic patient to prevent nocturnal seizures, or for those patients who experience migraine headaches on awakening, as well as for the debilitated patient for whom uninterrupted sleep is essential.

Another critical role for extended acting medications is in therapy of cardiovascular diseases whereby optimal peak blood levels of a medicament must be maintained at the steady state level to achieve the desired therapeutic effect. Unless conventional rapid acting drug therapy is carefully administered at frequent intervals to maintain effective steady state blood levels of the drug, peaks and valleys in the blood level of the active drug occurs because of the rapid absorption, systemic excretion of the compound and through metabolic inactivation, thereby introducing special problems in maintenance therapy of the patient. A further general advantage of longer acting drug preparations is improved patient compliance resulting from the avoidance of missed doses through patient forgetfulness.

The prior art teaching of the preparation and use of compositions providing the slow release of an active compound from a carrier is basically concerned with the release of the active substance into the physiologic fluids of the alimentary tract. However, it is generally recognized that the mere presence of an active substance into the physiologic fluids of the alimentary tract. However, it is generally recognized that the mere presence of an active drug substance in the gastrointestinal fluids does not, by itself, insure bioavailability. Bioavailability is the availability of a drug substance to the bloodstream and to the receptor site to achieve a desired pharmacologic action. Vioavailability, in a more meaningful sence, is the degree (or amount) to which a drug substance is absorbed to be available to a target tissue site after administration of a unit dosage form.

To be absorbed, an active drug substance must be in solution. The time required for a given proportion of an active drug substance contained in unit dosage form to enter into solution in appropriate physiologic fluids, is known as the dissolution time. The dissolution time of an active substance from a unit dosage form is determined as the proportion of the amount of active drug substance release from a unit dosage form over a specified time base by a test method conducted under standardized conditions. The physiologic fluids of the gastro intestinal tract are the media for determining dissolution time. The present state of the art recognizes many satisfactory test procedures to measure dissolution time for pharmaceutical compositions and these test procedures are described in official compendia world-wide.

Although there are many diverse factors which influence the dissolution of a drug substance from its carrier, the dissolution time determined for a pharmacologically active substance from the specific composition is relatively constant and reproducible. Among the different factors affecting the dissolution time are the surface area of the drug substance presented to the dissolution solvent medium, the pH of solution, the solubility of the substance in the specific solvent medium, and the driving forces of the saturation concentration of dissolved materials in the solvent medium. Thus, the dissolution concentration of an active drug substance is dynamically modified in its steady state as components are removed from the dissolution medium through absorption across the tissue site. Under physiologic conditions, the saturation level of the dissolved materials is replenished from the dosage form reserves to maintain a relatively uniform and constant dissolution concentration in the solvent medium providing for a steady state absorption.

The transport across a tissue absorption site of the gastrointestinal tract is influenced by the Donnan osmotic equilibrium forces on both sides of the membrane since the direction of this driving force is the difference between the concentrations of active substance on either side of the membrane, i.e., the amount dissolved in the gastrointestinal fluids and the amount present in the blood. Since the blood levels are constantly being modified by dilution, circulatory changes, tissue storage, metabolic conversion and systemic excretion, the flow of active materials is directed from the gastrointestinal tract into the bloodstream.

The prior art teaches that the absorption of drugs is influenced by the degree of electrical charges borne by the drug at the absorption site. Drugs which are present in an electrically uncharged form more readily cross the tissue absorption barrier than drugs in a dissociated or electrically charged state. Furthermore, the intrinsic oil-water partition coefficient for a substance which favors the oil phase is another characteristic leading to an increased rapid absorption of the drug substance across the alimentary tract and a slowed absorption of a drug substance is observed with an increased ionization strength of the substance. These relationships are well established in the art through findings that absorbable materials must pass through a lipoid-like barrier when penetrating membranes at the absorption site.

Notwithstanding the diverse factors influencing both dissolution and absorption of a drug substance, a strong correlation has been established between the in-vitro dissolution time determined for a dosage form and the in-vivo bioavailability. This correlation is so firmly established in the art that dissolution time has become generally descriptive of bioavailability potential for the active component of the particular unit dosage composition. In view of this relationship it is clear that the dissolution time determined for a composition is one of the important fundamental characteristics for consideration when evaluating slow release compositions.

SUMMARY OF THE INVENTION

This invention relates to pharmaceutical compositions with an extended and improved controlled rate of drug release providing for an extended bioavailability of the active materials incorporated therein. In particular, it provides for novel slow release compositions comprising a balanced combination of a salt of a pharmacologically active substance and the free active base moiety of said pharmacologically active salt in specific proportion to each other which, when incorporated into a slow release composition selectively modified the period of release of said pharmacologically active component from said slow release composition to materially affect the bioavailability of said pharmacologically active substance.

It is accordingly a primary object of this invention to provide a means to extend the period release of a pharmacologically active substance from a solid pharmaceutical dosage form by incorporating a balanced proportion of a salt of a pharmacologically active substance and the same pharmacologically active substance in its free base borne in said dosage form.

Still another object of this invention is to provide an improved method for manufacture of tablets containing pharmacologically active substance with particular reference to slow release compositions wherein tablet hardness interferes with packaging and transportation stresses.

Other objects and advantages of the present invention will be apparent from a further reading of the specification and of the appended claims.

With the above and other objects in view, the present invention mainly comprises an extended controlled release pharmaceutical composition comprising a slow release matrix having dispersed therein both the pharmacologically active salt form of a medication and the free base form of the same medication in a proportion of 25–75 parts by weight of said salt form to 25–75 parts by weight of said free base form, calculated with respect to the pharmacologically active non salt moiety.

It was unexpectedly found that the dissolution rate of a pharmacologically active substance from a slow release composition is materially extended when a balanced proportion of the pharmacologically active moiety in its free or base form is combined with the salt form of the substance in the slow release matrix. This extension of the dissolution time for this combination is not achieved through a use of larger amounts of the drug substances. In fact, essentially the same quantity of active drug is employed to obtain the extended effect through the use of the compositions of the present invention as is used for the earlier prior art preparations. Moreover the desired extension in dissolution time of a pharmacologically active moiety from a slow release preparation is not achieved through modification of either the carrier core, the retarding matrix or by altering any of the retardant coatings that may be used in the preparation. This effect is achieved through a preferential selective change in the inherent properties of the pharmacologically active substance of the composition to provide new dissolution characteristics in the physiologic fluids for the combination.

In order to obtain the desired extension in the dissolution time of a pharmacologically active moiety from a slow release preparation prepared with a salt of the pharmacologically active moiety, an amount of from 25% to 75% by weight of said salt is replaced with the free, or non-salt base of said pharmacologically active moiety. The combination of pharmacologically active salt and free base is then used as the active pharmacologic component in manufacture of the particular slow release preparation in the same manner as is known in the art to prepare the earlier slow acting dosage form.

It was found that, by appropriate selection of the ratio of base form to salt form of the active substance used as the active substance to manufacture a slow release preparation, different degrees of extension of the time for release of the active ingredient was obtained. The dissolution time was determined by the method described in USP XX, p. 959.

It was found in a test that when the dissolution time of a slow release preparation prepared with propranolol hydrochloride as the active ingredient was tested, 100% of the active material was released within 6 hours. However, when 50% by weight of the amount of propranolol contained in the propranolol hydrochloride was replaced with propranolol base, then the dissolution time was extended to 7 hours. When the ratio of propranolol salt to propranolol base is 40 parts by weight of salt and 60 parts by weight of propranolol base, the dissolution time determined for the preparation was approximately 10 to 12 hours.

In still another test a slow release antiarrhythmic tablet comprising quinidine polygalacturonate was formulated to provide a dissolution time of about 10 hours by methods known in the art. However, the dissolution time was materially extended by utilizing a combination of quinidine polygalacturonate and quinidine base. Thus if the combination active ingredient comprises 75% by weight of quinidine polygalacturonate and 25% by weight of quinidine base (based on quinidine equivalent content), the dissolution time is extended to 15 hours. When 40% by weight of the quinidine polygalacturonate is replaced with quinidine base, then the dissolution time for the preparation is extended to virtually 20 hours.

When a xanthine salt active ingredient, as for example, aminophylline or theophylline ethylenediamine, is used to prepare a slow release tablet in accord with the teaching of U.S. Pat. No. 3,965,256, all of the active material is released over the period of up to 9 hours. However, when theophylline base is used to replace 25% of the aminophylline (based on theophylline content equivalency) the dissolution time is extended to 12 hours.

The prior art teaches that absorption of an active drug across alimentary tract tissues is enhanced when the electrically charged form of the pharmacologically active substance is used rather than the electrically charged ionized form of the same substance. An opposite condition was unexpectedly found to occur with the new salt-base formulated dosage form since the presence of the electrically uncharged free base moiety caused a slowed dissolution time and extended bioavailability rather than a more rapid absorption.

Thus we find that the use of the electrically uncharged and lipid favoring base material does not accelerate dissolution time or stimulate absorption, and therefore increases bioavailability as taught in the prior art, but rather slows absorption and extends dissolution time and bioavailability. Then phenomenon is contrary to the present teachings of the prior art.

Moreover, solubility, per se, is not found to be a controlling factor as is also taught in the art, wince the same degree of extension in dissolution time and bioavailability was unexpectedly found when the combination salt-base active substance is used whether an insoluble salt or a soluble salt is combined with the appropriate base material. Thus we find that when the electrically uncharged codeine base is used to replace 50% of both the codeine content of codeine sulfate (solubility in water: 1:30) and codeine phosphate (solubility in water: 1:2), the bioavailability of both preparations is extended by approximately 12 hours. If solubility was the controlling factor in affecting the extension in the dissolution time and/or bioavailability, different values should have been found for the tablet preparation made with the more soluble salt codeine phosphate than that prepared with the less soluble sale, codeine sulfate.

While the invention is not meant to be limited to any specific theory as to why or how the extended release and increased bioavailability is obtained by using the combination of the salt form and free base form in the compositions of the invention, the following theory is given in the hope that it will help others in the further investigation of this field.

It appears that a new mechanism controls this unexpected phenomenon which involves the dynamic resonant interchange of ionizing salt moiety and electrically uncharged base moiety. When a salt is incorporated in a slow release carrier, the total number of particles released into the physiologic fluids comprise both dissociated and undissociated materials which give rise to a constant dissolution time for the formulation and which is correlatable to the bioavailability for the preparation. However, when the free base replaces a proportion of the salt, a shift in the ratio of the charged to uncharged particles in solution occurs and thus slows the availability of active moiety at the absorption site since there is now a disproportionate composition of salt to base moieties in solution with greater competition for the electrically charged ions by the electrically neutral base particles, thereby altering the entire equilibrium of the system. This shift in equilibrium is reflected in the extended dissolution time and consequent extended bioavailability to result in materially new and advantageous properties for the composition.

Slow release tablets and capsules utilizing the new combined salt-base active ingredient may be prepared with the matrix and other carriers used for this purpose which are known in the art. Thus, tablet cores intended for special coatings as a means to retard the release of active ingredient may be prepared with the new salt-base active ingredient to result in a further extension of the bioavailability of the active ingredient used alone in the same vehicle. Preferred slow release pharmaceutical compositions utilizing the new combined salt-base active ingredient may be prepared with the sustained release matrix comprising hydroxyalkylcellulose components and higher aliphatic alcohols as described in U.S. Pat. No. 4,235,870. By utilizing the appropriate proportions of from 25% to 75% of base to salt, an extension of from 3 to 15 hours in the already delayed release of the active ingredient is obtained. Such extended duration in dissolution time enables optimal bioavailability of the active therapeutic agent over a sufficient duration to permit one-a-day medication.

Among the preferred pharmacologically active base substances which are suitable for the preparation of slow release tablets and capsules utilizing the new combined salt-base mechanism are those listed in Table I.

TABLE I

SOME PREFERRED BASE ACTIVE SUBSTANCES USEFUL IN THE PREPARATION OF SLOW RELEASE COMPOSITIONS

| | |
|---|---|
| Amitryptaline | Morphine |
| Atropine | Oxycodone |
| Chlorpheniramine | Papavarine |
| Chlorpromizine | Phenylpropanolamine |
| Codeine | Propranolol |
| Dexbrompheniramine | Quinidine |
| Diphenylhydramine | Scopolamine |
| Doxilamine | Theophylline |
| Ephedrine | Theophylline |
| Ephedrine | Thioridazine |
| Hyoscyamine | |

The substances described in Table I above are representative of pharmacologically active classes of compounds which are desirable for dispensing in the form of a slow release composition intended to provide an active pharmacologic effect over an extended period. When preparing slow release preparations with the base substances described in Table I, these base substances are used to replace a proportion of from 25% to 75% by weight of the amount of the pharmacologically active salt of said base which would be ordinarily used to prepare a slow release tablet or capsule preparation.

In practice, the appropriate salt-base combination used as the active ingredient is intimately mixed, with both the salt and the base being preferably of the same particle size. As a general rule a particle size of about 20–60 US Standard Mesh Screen size will be found to be an optimal particle size for this purpose. The powdered salt-base active ingredient is then utilized in the same manner as in the preparation of conventional slow release tablet or capsule preparations. Thus the active ingredient is added to the carrier materials at the indicated step in the process as are known to the art when the core tablet to be used for coating is manufactured.

When a slow release tablet matrix is used as a vehicle for the salt-base active ingredient, then the combination powdered active ingredient is added to the composition at the appropriate step in the manufacturing process as though it consisted of the salt alone. However, the unique properties of the salt-base formulation enables modification in the teachings of the art in the manufacture of slow release tablets and capsules utilizing a matrix. Thus, in the manufacture of an antiarrhythmic slow release tablet employing quinidine polygalacturonate and quinidine base in proportions of 60 parts by weight of salt to 40 parts by weight of base as the active ingredient, the following manufacturing method will be found to be satisfactory.

| | (%) Parts by Weight |
|---|---|
| Quinidine Polygalacturonate | 56.8 |
| Quinidine Base | 22.9 |
| Hydroxyethylcellulose | 6.4 |
| Stearyl alcohol | 12.8 |

| -continued | |
|---|---|
| | (%) Parts by Weight |
| Lubricants (Silicon dioxide) | 1.1 |
| | 100.0 |

In this formula 60% of the quinidine content is represented by quinidine polygalacturonate and 40% by quinidine base.

Step 1: Intimately mix the appropriate quantity of quinidine polygalacturonate and quinidine base and pass through a No. 20 US Standard Mesh Screen and add the necessary quantity of hydroxyethylcellulose and blend to obtain a uniform composition.

Step 2: Hydrate the mixture of Step 1 with from 2 to 4 parts by weight of water for each part by weight of cellulose component used in Step 1 with a preferred ratio being 3:1 parts by weight. Stir the granular paste until uniform.

Step 3: Dry the mass and pass through a No. 16 US Standard Mesh Screen.

Step 4: In a separate vessel melt the stearyl alcohol and add the granules obtained as a result of Step 3 to the molten alcohol.

Step 5: Cool to room temperature and pass the granules of Step 4 through a No. 12 or No. 14 US Standard Mesh Screen. Add appropriate lubricants and compress into tablets of suitable size and shape.

Final tablet weight 360.0 mgm.
Tablet diameter 13/32 inch
Harness 8 kg stokes
Quinidine content per tablet 206.0 mgm.

When capsules are desired as the slow release unit dosage form, then the composition obtained prior to the compression tableting Step 5, described above, is filled into capsules of appropriate size, shape and weight.

This manufacturing procedure may be used to prepare a slow release preparation with propranolol hydrochloride/propranolol base; codeine phosphate/codeine base; aminophylline/theophylline, as well as slow release tablets and capsules prepared with the base materials in Table I utilizing either the hydrochloride, sulfate or maleate salts of the respective base active substances listed in Table I.

When preparing slow release unit dosage forms with the base substances described above (Table I), the active base materials may be used to replace from 25% to 75% by weight of the amount of the corresponding salt which is ordinarily used to prepare a slow release tablet or capsule preparation. When the new combined salt-base active ingredient is used, an extension of the dissolution time for the product normally obtained for the particular vehicle will be extended by a period of at least 3 hours, when from 25% to 75% by weight of the active ingredient salt is replaced with the particular base. When from 60% to 75% by weight of the pharmacologically active salt is replaced with the indicated base of the active salt ingredient, then an extension in the dissolution time of from 10 to 14 hours and even longer periods, is observed. When a 50/50 mixture of the salt-base active ingredient is used, the usual extension dissolution time over that observed when the salt form is used, alone, is approximately 5 hours. Thus, by appropriate adjustment of the proportion of the amount of the salt form of the active ingredient being replaced with the respective base, a broad range in the extension of the observed dissolution time and corresponding bioavailability for the active ingredient occurs to provide a flexibility to meet the required therapeutic needs of the particular base as well as to provide a means to achieve one-a-day therapy.

It was further unexpectedly found that when an organic salt is used to formulate the slow release tablet, that the new combination salt-base active ingredient permitted the preparation of a tablet of smaller size with an improved tablet hardness. Thus when quinidine polygalacturonate is utilized to prepare a slow release tablet in accord with the teachings of U.S. Pat. No. 3,965,256, the resultant slow release tablet has a tablet hardness characteristic determined by the Stokes Hardness Testor of 4 kg. This value is at the lower limit of acceptable hardness and inherently leads to increased tablet friability, but when the combined salt-base active ingredient of the present invention is used in the appropriate proportions, a tablet with a hardness value of 7 to 8 kg. is obtained without altering the disintegration time of the tablet and without increasing tablet size or the need for added binders.

Tablet hardness is the term used to describe the resistance of a tablet to chipping, erosion, abrasion and breakage under conditions of storage, transportation and handling. A tablet is considered to be of proper hardness when a clean break is achieved when snapped between the second and third fingers, using the thumb as a fulcrum and further, if the tablet does not break when dropped from a height of at least 3 feet. If the tablet is too hard, it will not disintegrate within the required time period to release the active ingredients. If it is too soft, it will not withstand the handling durations during packaging, as well as the mechanical stress of shipping and distribution.

There have been many methods introduced to quantitate the characteristic of tablet hardness and several instrumental methods are utilized for this purpose. These instruments measure the force required to break a tablet when the generated force is applied diametrically to the tablet. This force is expressed in kg. Such instruments as the Stokes Hardness Testor (available from Stokes Division, Pennwalt Corp., Rochester, N.Y.) the Strong Cobb Hardness Testor (available from Strong Cobb-Arner, Inc., Cleveland, Ohio) and the Pfizer Hardness Testor (distributed by Pfizer Inc., New York, N.Y.) are all well known articles of commerce. All of these instruments utilize the common principle of measuring the force required to break a tablet when the generated force is applied diametrically to the tablet and this force is expressed in kg. These instruments have been equilibrated to one another and generally have a correlation factor to be applied to the instrumental results to enable common interpretation of the determined tablet hardness. A tablet hardness of 4 kg. is generally considered to be the minimum level for a satisfactory tablet and a tablet hardness of above 9 kg. is generally considered to be unsatisfactory since inappropriate disintegration time occurs.

The problem of tablet hardness is frequently encountered when active ingredients comprising organic salts such as gluconates, polygalacturonates, tannates, maleates, high fatty acids as for example, the alkyl fatty acids having a carbon chain length of from 8 to 18 carbon atoms, or aromatic acids as for example, benzoates, salicylates and phthalates are used to prepare slow release tablets. Although appropriate binders may be added to correct this problem, the tablet size increases proportionately to present new problems in swallowing the tablet. If the compression force is increased to produce a harder tablet, the disintegration time of the tablet is adversely affected to result in unsatisfactory values. This problem of tablet hardness is especially encountered in the preparation of the tablet core intended to be coated with a slow release coating, since the soft tablet core will not withstand the tumbling compression encountered in the coating step. Consequently a high order of tablet rejection results even approaching 20% of the batch when the core has a tablet hardness of about 4 kg. When a lipophilic/hydrophobic tablet matrix is used to prepare a slow release preparation, the inherent nature of the wax materials often results in a soft tablet. Such tablets require special handling thereby increasing costs of manufacture and shipping.

It was unexpectedly found that when a proportion of the organic salt used as the active substance is replaced with the same active base moiety, the characteristic of tablet hardness was advantageously improved without affecting the disintegration time or tablet size. Thus for example, when quinidine polygalacturonate is used to prepare slow release pharmaceutical compositions comprising a hydrated hydroxyalkylcellulose and higher fatty alcohol in accord with the method of Examples 1 and 7 of U.S. Pat. No. 3,965,256 (patented June 22, 1976), the tablet hardness measured by the Stokes Hardness Testor is 4 kg. This tablet exhibits about 15% chipping and friable erosion during packaging, thus requiring costly special handling. When added tablet excipients and binders are utilized to increase tablet hardness to 6 kg. as measured by the Stokes Tablet Hardness instrument, a tablet of extraordinary size results. However, when at least 10% by weight of the amount of quinidine polygalacturonate present in the formulation is replaced with quinidine base, the tablet hardness is appreciably and favorably improved without materially affecting the disintegration time of tablet size. When optimal proportions of base to salt, as for example the ratio of from 25% to 35% by weight of the quinidine base to from 65% to 75% of the salt is used, this results in a tablet hardness of about 7 to 10 kg. (Stokes). Furthermore, such slow release tablet now has less than 0.01% chipping and erosive friability during manufacture, handling and shipping. Similar favorable results are obtained when a proportion of other organic salts which are used as the active ingredient is replaced with the base moiety.

When it is desired to utilize the new slow release compositions in therapy, the dosage form may be either a tablet or a capsule and the particular salt-base replacement proportions will depend on the preferred specific therapeutic needs. When it is desired to utilize one-a-day therapy dosage schedules, then it will be found useful to replace 75% of the pharmacologically active salt used as the therapeutic ingredient with the base moiety and in certain instances it may be desired to use even a higher base salt replacement ratio of up to 90% of the amount of the salt used being replaced by the base. The exact proportion of active salt replaced by the base is dependent on the duration of bioavailability desired to be achieved with the particular dosage form. A particular advantage of the present slow release composition is obtained by adjusting the proportion of salt/base active ingredient in slow release pharmaceutical compositions to obtain the desired bioavailability for one-a-day administration schedules of a therapeutic dosage form, without materially modifying tablet size or increasing the amount of active ingredients.

DESCRIPTION OF THE PREFERRED EMBODIMENTS

The following examples are given to further illustrate the present invention. The scope of the invention is not, however, meant to be limited to the specific details of the examples:

The general method utilized in the production of the composition of the present invention is set forth below:

To further extend the dissolution time of an active ingredient from a slow release tablet or capsule composition prepared with a pharmacologically active salt, from 25% to 75% of the amount of pharmacologically active salt used in the formula is replaced with the free active base moiety of said salt. When selecting the quantity of the pharmacologically active salt to be replaced with the base, the pharmacologically active portion of the salt enters into such determination. For example, if the active salt used is theophylline ethylenediamine, which is also known as aminophylline, and it is desired to replace from 25% to 75% of the active base moiety of the salt, then the calculations are based on the theophylline content of the quantity of aminophylline used to prepare the slow release tablet intended to be extended, and the weight of the ethylenediamine portion is disregarded.

Thus all replacement steps described in accord with the present method to further extend the dissolution time of an active ingredient used in a slow release tablet is based on the quantity of pharmacologically active moiety of the product, not the overall weight of the active salt, per se. The new base salt combination is used as the single active ingredient when calculating the active ingredient weights in tablet or capsule dosage forms.

When utilizing the combination of pharmacologically active salt and active base, the materials are intimately mixed and preferably granulated through a No. 16 US Standard Mesh Screen. In practice, it will be found convenient to combine the mixing and granulating steps with other ingredients in the manufacture of slow release preparations. When the salt base active ingredient is incorporated into the tablet core, it is preferably mixed with the indicated diluents in the same order and sequence as would be used in the manufacture of the tablet had the single salt active ingredient been used. The finished tablet core is then coated with an appropriate release retarding coating.

When a balanced matrix comprising a hydrophilic cellulose component and a hydrophobic alcohol wax component is used as the carrier for the active ingredient of an uncoated slow release tablet, then the combination of the salt base active materials is preferably mixed with the hydrophilic components, including the other appropriate diluents, before the mixture is granulated. While it is preferred that the active salt base components be included with the hydrophilic ingredients, as for example, cellulose, lactose, starch and povidone, it may be found useful in certain instances to incorporate the active salt base composition with the hydrophobic components as for example, the fatty alcohols and waxes which are used to prepare the slow release matrix.

The following method is useful to obtain an extension of the dissolution time of the active ingredients of a slow release tablet.

Step 1: Intimately mix the appropriate quantities of the pharmacological active salt and its free active base together with the cellulose component and other hydrophilic diluents, such as lactose, starch and povidone as may be required.

Step 2: Hydrate the mixture of Step 1 with from 2 parts by weight to 4 parts by weight of water for each part by weight of cellulose component and stir to form a granular paste. If other hydrophylic polymers are present, then slightly less water should be used as for example, 2-3 parts by weight of water.

Step 3: Dry the mixture and granulate through a No. 16 US Standard Mesh Screen.

Step 4: Melt the hydrophobic components as for example, a fatty alcohol of from 10 to 18 carbon atoms in chain length, waxes, petroleum waxes and mixtures of these and add the melt to the granules obtained from Step 3 above. The mixture should be well stirred until uniform.

Step 5: Allow the coated granules to cool to room temperature and granulate through a No. 12 or No. 14 US Standard Mesh Screen.

Step 6: Add the appropriate lubricants to the granules of Step 5 and compress into tablets of desired shape, size and weight.

The dissolution time determined for such slow release tablets will be significantly slowed to enable a wide range of therapeutic dosage flexibility, including one-a-day regimens.

Should it be desired to utilize capsule dosage forms, then the mixtures obtained prior to tablet compression are filled into appropriate capsules and the whole coated with a retarding coat in the manner well known to the art.

EXAMPLE 1

When it is desired to further retard the dissolution time of the active quinidine content from a quinidine polygalacturonate slow release tablet, then a slow release tablet of the following composition is prepared:

| Tablet A | Parts by Weight (%) |
|---|---|
| Quinidine Polygalacturonate | 56.8 |
| Quinidine Base | 22.9 |
| Hydroxyethylcellulose | 6.4 |
| Stearyl alcohol | 12.8 |
| Tablet Lubricants | 1.1 |
| | 100.0 |

In this formulation, 60% of the active quinidine content for the tablet is contributed by the salt, quinidine polygalacturonate, and 40% of the quinidine content of the tablet is contributed by quinidine base.

The following method is used to manufacture the slow release tablets:

Step 1: Intimately mix the quinidine polygalacturonate and quinidine base and add the hydroxyethylcellulose; continue mixing until uniform.

Step 2: Hydrate the mixture of Step 1 with sufficient water to form a granular paste. From 2-4 parts by weight of water for each part by weight of the cellulose material will be found to be sufficient.

Step 3: Dry the mixture and granulate through a No. 16 US Standard Mesh Screen.

Step 4: Melt the stearyl alcohol and coat the prepared granules with the melted fatty alcohol; mix well to obtain a uniform coating.

Step 5: Allow the coated granules to cool and granulate through a No. 12 or No. 14 US Standard Mesh Screen.

Step 6: Add the appropriate lubricants and compress into tablets of desired size, shape and weight, as follows:
Final tablet weight = 360.0 mgm.
Tablet diameter = 13/32"
Hardness: 8 kg (Stokes)
Quinidine content per tablet—206.0 mgm.

The dissolution time determined for this slow release tablet establishes that the release of 100% of active quinidine content occurs over 20 hours.

When a slow release tablet is prepared with the same carrier but utilizing only the salt, quinidine polygalacturonate, as the active ingredient, as for example:

| Tablet B | Parts by Weight (%) |
|---|---|
| Quinidine Polygalacturonate | 77.0 |
| Hydroxyethylcellulose | 7.0 |
| Stearyl alcohol | 14.0 |
| Tablet Lubricants | 2.0 |
| | 100.0 |

Tablet Compression Data
Final tablet weight = 442.6
Diameter of tablet - 14/32"
Hardness: 4 kg (Stokes)
Quinidine content per tablet - 206.0 mgm.

and utilizing the same method of manufacture as described above, the dissolution time for 100% of the quinidine content to be released is 12 hours.

A comparison of the dissolution rates determined for both tablets is as follows:

| | Tablet A Quinidine Poly- galacturonate Quinidine Base (60:40) | Tablet B Quinidine Polygalac- turonate 100% |
|---|---|---|
| | % Quinidine Content Released | |
| 1 hour in simulated gastric juice | 26% | 18% |
| 2 hours in simulated intestinal juice | 31% | 24% |
| 3 hours in simulated intestinal juice | 36% | 33% |
| 4 hours in simulated intestinal juice | 40% | 43% |
| 6 hours in simulated intestinal juice | 51% | 61% |
| 9 hours in simulated intestinal juice | 69% | 82% |
| 12 hours in simulated intestinal juice | 90% | 100% |
| 18 hours in simulated intestinal juice | 93% | — |
| 20 hours in simulated intestinal juice | 100% | — |

It will be seen that the replacement of 40% of the amount of the quinidine present in the salt quinidine polygalacturonate, used to prepare the tablets of Formula B, with quinidine base (Formula A) results in an extension of the dissolution time by approximately 8 hours over that determined for the salt formulation (Formula B) to achieve the 100% release of active ingredient. This order of extended dissolution time of 20 hours for the release of the active ingredient enables a one-a-day regimen for the administration of quinidine therapy to control an arrhythmic heart beat.

The tablet hardness of 4 kg (Stokes) obtained for the slow release tablet utilizing 100% of the organic salt, quinidine polygalacturonate, as the active ingredient (Formula B) is improved to provide a tablet hardness of 8 kg (Stokes) when the Formula A, wherein 40% by weight of the amount of quinidine in the salt active ingredient replaced with quinidine base, is used. This improved tablet hardness overcomes problems of packaging and transport tablet friability.

EXAMPLE 2

To extend the dissolution time of a slow release tablet containing propranolol hydrochloride as the active ingredient, the following formula is used:

| Formula A | Parts by Weight |
|---|---|
| Propranolol HCl | 22.0 |
| Propranolol base | 34.0 |
| Lactose | 4.8 |
| Hydroxyethylcellulose | 5.2 |
| Paraffin Wax | 28.2 |
| Lubricants (Talc, Magnesium Stearate) | 2.0 |
| | 100.0 |

In the above Formula A, about 40% of the propranolol content of the tablet is present as propranolol HCl and about 60% as propranolol base. The method of manufacture for these tablets is as follows:

Step 1: Mix the propranolol HCl, lactose and propranolol base together with the hydroxyethylcellulose utilizing a suitable mixer.

Step 2: Hydrate the mixture of Step 1 with sufficient water to obtain a granular paste utilizing from 2 to 4 parts by weight of water for each part by weight of hydroxyethylcellulose.

Step 3: Dry the mixture and granulate through a No. 16 US Standard Mesh Screen.

Step 4: Melt the paraffin wax and add to the prepared granules of Step 3 to coat the granules.

Step 5: Allow the coated granules to cool and granulate through a No. 12 or No. 14 US Standard Mesh Screen.

Step 6: Add the appropriate tablet lubricants and compress into tablets of the following size, shape and weight:
Final tablet weight—124.0 mg.
Tablet diameter=9/32"
Propranolol content per tablet—70 mgm.

In order to demonstrate the degree of extension of the dissolution time obtained when propranolol base is used to replace a proportion of the active ingredient salt, propranolol hydrochloride, slow release tablets utilizing the same matrix and the same method of manufacture, but only the salt, propranolol hydrochloride, as the active ingredient, were prepared as the following Formula B:

| Formula B | Parts by Weight (%) |
|---|---|
| Propranolol HCl | 64.5 |
| Hydroxyethylcellulose | 5.2 |
| Paraffin Wax | 28.3 |
| Lubricants (Talc, Magnesium Stearate) | 2.0 |
| | 100.0 |

Tablet Compression Data
Final tablet weight = 124.0 mg.
Tablet diameter = 9/32"
Propranolol content per tablet - 70 mgm.

Side-by-side comparative dissolution time requirements for the respective tablets were determined with the following results:

| After: | Tablet A Propranolol HCl Propranolol base (40:60) | Tablet B Propranolol HCl (100%) |
|---|---|---|
| | % Propranolol Released | |
| 1 hour in simulated gastric juice | 38% | 35% |
| 2 hours in simulated intestinal juice | 55% | 57% |
| 3 hours in simulated intestinal juice | 63% | 68% |
| 4 hours in simulated intestinal juice | 68% | 83% |
| 5 hours in simulated intestinal juice | 73% | 93% |
| 6 hours in simulated intestinal juice | 76% | 100% |
| 9 hours in simulated intestinal juice | 100% | — |

The salt base combination active ingredient extends the dissolution time for propranolol in the slow release tablet, from 6 hours when 100% of the active ingredient is in the salt form, to 9 hours when 60% of the salt has been replaced by the base.

EXAMPLE 3

When it is desired to prepare an extended slow release tablet with xanthine active ingredient, as for example, theophylline, to accomplish a one-a-day dosage regimen, then the following procedure is preferred.

Aminophylline is a well known water soluble salt of theophylline which is commonly used to prepare theophylline-containing slow release preparations. In such a formula 30% by weight of the theophylline content of the extended slow release tablet is contributed by aminophylline and the remaining 70% by weight of the theophylline content of the tablet is in the form of theophylline base, so that the total amount of theophylline per tablet is 280 mg. The formula and method of manufacture for such extended release tablets are as follows:

| Formula A | Parts by Weight (%) |
|---|---|
| Aminophylline | 24.0 |
| Theophylline | 45.6 |
| Hydroxyethylcellulose | 6.2 |
| Polyvinylpyrrolidone | 1.0 |
| Cetostearyl alcohol | 20.6 |
| Lubricants (Talc, Magnesium Stearate) | 2.6 |
| | 100.0 |

Step 1: Mix the appropriate quantity of aminophylline with the hydroxyethylcellulose.

Step 2: Dissolve the indicated quantity of polyvinylpyrrolidone in a sufficient quantity of water equivalent to from 2.4 parts by weight of water for each part by weight hydroxyethylcellulose, used in Step 1, above, and add the solution to the solid mixture obtained from Step 1, mixing well until a granular paste forms.

Step 3: Dry the mixture and granulate through a No. 16 US Standard Mesh Screen.

Step 4: Melt the cetostearyl alcohol and coat granules prepared with the melted fatty alcohol.

Step 5: Allow the coated granules to cool and granulate through No. 12 or No. 14 US Standard Mesh Screen.

Step 6: Add the appropriate lubricants and press into tablets of desired shape, size and weight, as follows:
Final tablet weight=430.9 mg.
Final tablet diameter=14/32"
Theophylline content per tablet—280 mg.

Tablet hardness: 12 kg

The dissolution time determined for Formula A consisting of (30:70 salt:base) is 24 hours. When aminophylline is the sole active ingredient (100% salt) the dissolution time is determined to be approximately 9 hours. When 25% of the theophylline content of the salt, aminophylline, is replaced with theophylline base, then the dissolution time is extended to approximately 12 hours. Side-by-side dissolution time values for the separate aminophylline salt/theophylline base slow release tablets are as follows:

|  | Xanthine Slow Release Tablets | | |
| --- | --- | --- | --- |
|  | Aminophylline (100% Salt) | Salt 75% Base 25% | Salt 30% Base 70% |
|  | % Theophylline Released | | |
| 1 hour in simulated gastric juice | 15.5 | 10.0 | 9.2 |
| 2 hours in simulated intestinal juice | 30.1 | 20.2 | 18.0 |
| 3 hours in simulated intestinal juice | 42.7 | 29.6 | 25.8 |
| 4 hours in simulated intestinal juice | 51.7 | 39.1 | 31.6 |
| 6 hours in simulated intestinal juice | 61.3 | 54.2 | 42.0 |
| 9 hours in simulated intestinal juice | 100.0 | 79.1 | 55.1 |
| 12 hours in simulated intestinal juice | — | 100.0 | 67.0 |
| 15 hours in simulated intestinal juice | — | — | 76.1 |
| 18 hours in simulated intestinal juice | — | — | 86.0 |
| 21 hours in simulated intestinal juice | — | — | 95.2 |
| 24 hours in simulated intestinal juice | — | — | 100.0 |

Thus it will be seen that a new degree of therapeutic flexibility results with the new method for xanthine dosage preparations as for example, theophylline compositions since by appropriate salt to base ratio of the xanthine content of a particular slow release product, a wide range in therapeutic effects as demonstrated by dissolution time will be achieved, to meet the individual patients needs including one-a-day administration.

EXAMPLE 4

To further extend dissolution time of codeine from a slow release codeine phosphate tablet, containing a codeine content equivalent to 60 mg. codeine per tablet, the following formula is used:

| Formula A | Parts by Weight (%) |
| --- | --- |
| Codeine Phosphate | 29.6 |
| Codeine Base | 22.3 |
| Hydroxyethylcellulose | 6.0 |
| Cetrostearyl alcohol | 23.8 |
| Lactose | 16.3 |
| Lubricants (Talc, Magnesium Stearate) | 2.0 |
|  | 100.0 |

In this formulation the codeine content is equally contributed by equal parts of codeine phosphate, (the salt,) and codeine base (50:50 base/salt). The improved extended dissolution time slow release tablets are manufactured as follows:

Step 1: Mix indicated quantities of codeine phosphate and codeine base with the lactose.

Step 2: Add the appropriate quantity of hydroxyethylcellulose to the mixture obtained from Step 1, and hydrate with from 2 parts by weight to 4 parts by weight of water for each part by weight of hydroxyethylcellulose until a granular paste is obtained.

Step 3: Dry the hydrated mixture and granulate through a No. 16 US Standard Mesh Screen.

Step 4: Melt the cetostearyl alcohol and add to the granules obtained from Step 3 until a uniform distribution is obtained, and set aside to cool to room temperature.

Step 5: Granulate the mixture of Step 4 through a No. 12 or No. 14 US Standard Mesh Screen.

Step 6: Add appropriate lubricants and compress into tablets of the following size, shape and weight:
Tablet weight = 134.5 mgm.
Codeine Content per tablet = 60 mg.
Tablet diameter—9/32"

The dissolution time for the codeine phosphate/codeine base (50:50 ratio) is 7 hours for 100% of the codeine content of the tablet to be released. This value represents an extension of twice the dissolution time obtained when 100% salt is used as the active ingredient, as for example, codeine phosphate, in the same tablet matrix, for which formula the dissolution time to release 100% of the codeine content is 3.5 hours. This is demonstrated when side-by-side dissolution time testing is conducted.

A slow release tablet was prepared with codeine phosphate as the sole active ingredient, in an amount sufficient to provide 60 mg. of codeine content per tablet utilizing essentially the same matrix formula as Formula A, above:

| Formula B | Parts by Weight (%) |
| --- | --- |
| Codeine Phosphate | 59.5 |
| Hydroxyethylcellulose | 6.0 |
| Lactose | 8.8 |
| Cetostearyl alcohol | 23.7 |
| Lubricants (Talc, Magnesium Stearate) | 2.0 |
|  | 100.0 |

The tablets were manufactured in essentially the same steps as that described above. The slow release tablets were compressed to the following description:
Tablet weight = 134.5 mg.
Codeine Content per tablet = 60 mg.
Tablet diameter—9/32"

The side-by-side dissolution time was determined for both tablets using the U.S.P. paddle method, to yield the following results:

| After: | Tablet A Codeine Phosphate/ Codeine Base (50:50) | Tablet B Codeine Phosphate (100%) |
| --- | --- | --- |
|  | % Codeine Released | |
| 1 hour in simulated gastric juice | 46% | 58% |
| 2 hours in simulated intestinal juice | 67% | 82% |
| 3 hours in simulated intestinal juice | 79% | 96% |
| 3.5 hours in simulated intestinal juice | 88% | 100% |
| 5 hours in simulated intestinal juice | 92% | — |
| 6 hours in simulated intestinal juice | 95% | — |
| 7 hours in simulated intestinal juice | 100% | — |

The salt-base active ingredient extended the dissolution time of codeine from the slow release tablet of the same compositions by 100% without requiring increasing amounts of matrix components or other formula changes.

The bioavailability study of Tablet A comprising codeine phosphate/codeine base (50:50) demonstrated that satisfactory blood levels were maintained over a period of 7 hours thus confirming that extended bioavailability follows dissolution time.

EXAMPLE 5

In place of the hydroxyethylcellulose as used above, there may be substituted in equal amounts, hydroxymethylcellulose, hydroxypropylcellulose and mixtures of these.

In place of the fatty alcohol used as described above, there may be substituted in equivalent amounts any one of the higher aliphatic alcohols having from 10 to 18 carbon atoms in chain length and mixtures of these. Such aliphatic alcohols such as cetostearyl alcohol may be substituted in equal quantities for the cetyl alcohol as described above.

Lauryl alcohol, myristyl alcohol and stearyl alcohol are preferred alternate alcohols to the cetyl alcohol used as described above. In each and every instance wherein a fatty alcohol is used, an equivalent amount of paraffin wax may be substituted.

When these alternate hydrophilic and hydrophobic components are utilized in a slow release formulation, the manufacturing procedures described for the particular tablet remains the same and the resulting tablet will behave in essentially the same manner as described above.

EXAMPLE 6

The present method providing for the use of a pharmacologically active combination of a salt and base as an active ingredient to extend the dissolution time of slow release tablets provides a wide degree of flexibility in the therapeutic regimen for patients requiring extended bioavailability of a therapeutic agent. Thus, improved blood levels for extended periods of time results when the tablet compositions described in Examples 1-5 above are administered to a human or animal from 1 to 4 times daily after appropriate selection of the desired ratio of active base moiety to active pharmacologic salt as the active ingredient.

When the ratio of active base to salt is up to equal parts of each, the dissolution time extension is of a lesser magnitude than that obtained when the proportion of salt to base is greater than 50:50. The exact ratio to use to obtain a particular extension in dissolution time depends upon the particular active ingredient as well as the patients therapeutic needs.

While the invention has been described with respect to the production of certain specific compositions, it is apparent that variations and modifications of the invention can be made without departing from the spirit or scope of the invention.

What is claimed is:

1. On an extended action controlled release pharmaceutical composition for oral administration comprising a hydrated hydroxyalkylcellulose and hydrophobic 10 to 18 carbon atoms higher aliphatic alcohol or paraffin wax balanced matrix melt granulation pharmaceutically acceptable controlled release core or matrix for the oral administration of pharmaceutically active agents, said controlled release core or matrix providing upon oral ingestion thereof slow release in the body of pharmaceutically active agents distributed therein, the improvement wherein said composition comprises said controlled release core or matrix for oral administration having distributed therethrough a pharmaceutically effective amount of a pharmacologically active substance in salt form thereof and in the free base form thereof, said pharmaceutically effective amount comprising between about 75% and 25% by weight of a pharmaceutically acceptable salt form of said pharmacologically active substance and between about 25% and 75% by weight of the free base form of said pharmacologically active substance, the amounts being based on the pharmacologically active moiety of said pharmacologically active substance.

2. Extended action controlled release composition according to claim 1 wherein said composition is in tablet form.

3. Extended action controlled release pharmaceutical composition according to claim 1 wherein said composition is in capsule form.

4. Extended action controlled release pharmaceutical composition according to claim 1 wherein the pharmacologically active substance is amitryptaline, atropine, chlorpheniramine, chlorpromizine, codeine, dexbrompheniramine, diphenylhydramine, doxilamine, ephedrine, hyoscyamine, morphine, oxycodone, papavarine, phenylpropanolamine, propranolol, quinidine, scopolamine, theophylline or thioridazine.

5. Composition according to claim 1 in tablet form.

6. Composition according to claim 5 in capsule form.

7. Composition according to claim 1 wherein the pharmaceutically effective amount of said pharmacologically active substance comprises between about 60% and 40% by weight of the salt form and about 40%-60% by weight of the free base form.

8. Extended action controlled release pharmaceutical composition according to claim 1 wherein said controlled release core or matrix for oral administration has distributed therethrough quinidine base and quinidine polygalacturonate or propranolol base and propranolol hydrochloride or theophylline and aminophylline or codeine base and codeine phosphate.

9. Extended action controlled release pharmaceutical composition according to claim 1 wherein said controlled release core or matrix for oral administration has distributed therethrough codeine base and codeine phosphate.

* * * * *